United States Patent
Doets

[11] Patent Number: 6,059,833
[45] Date of Patent: May 9, 2000

[54] ELLIPTIC ACETABULAR COMPONENT FOR A HIP PROTHESIS

[75] Inventor: Hendrik Cornelis Doets, Amsterdam, Netherlands

[73] Assignee: Endocare AG, Switzerland

[21] Appl. No.: 08/652,568

[22] PCT Filed: Dec. 16, 1994

[86] PCT No.: PCT/EP94/04193

§ 371 Date: Sep. 18, 1996

§ 102(e) Date: Sep. 18, 1996

[87] PCT Pub. No.: WO95/16413

PCT Pub. Date: Jun. 22, 1995

[30] Foreign Application Priority Data

Dec. 16, 1993 [NL] Netherlands ............................ 9302200

[51] Int. Cl.[7] .................................. A61F 2/32; A61F 2/36
[52] U.S. Cl. ................................................ 623/22; 623/23
[58] Field of Search .......................................... 623/22, 23

[56] References Cited

U.S. PATENT DOCUMENTS

| | | | |
|---|---|---|---|
| 4,666,448 | 5/1987 | Ganz | 623/22 |
| 4,878,916 | 11/1989 | Rhenter et al. | 623/18 |
| 4,878,946 | 11/1989 | Rhenter et al. | 623/22 |
| 5,021,062 | 6/1991 | Adrey et al. | 623/22 |
| 5,171,285 | 12/1992 | Broderick | 623/22 |
| 5,226,917 | 7/1993 | Schryver | 623/22 |
| 5,549,695 | 8/1996 | Spotomo et al. | 623/22 |

*Primary Examiner*—Mickey Yu
*Assistant Examiner*—Alvin Stewart
*Attorney, Agent, or Firm*—Andrus, Sceales, Starke & Sawall

[57] ABSTRACT

A hip cup for use as an acetabular component in a hip prosthesis including a shell part having a partially convex outer surface. The shell part is insertable in a cavity having an inner surface that is substantially defined by the outer surface of a segment of a sphere. The outer surface of the shell part substantially corresponds to the outer surface of a part of an ellipsoid and has an apex. During positioning of the shell part in the cavity, the shell part has a circumferential edge contacting the longitudinal edge of the cavity, with a space formed between the inner surface of the cavity and the apex of the shell part. A tool has an end releasably attachable to the shell part and a striking end. A handle on the tool permits positioning the tool and shell part to the cavity and striking the end to enact the shell in the part in a selected position.

13 Claims, 3 Drawing Sheets

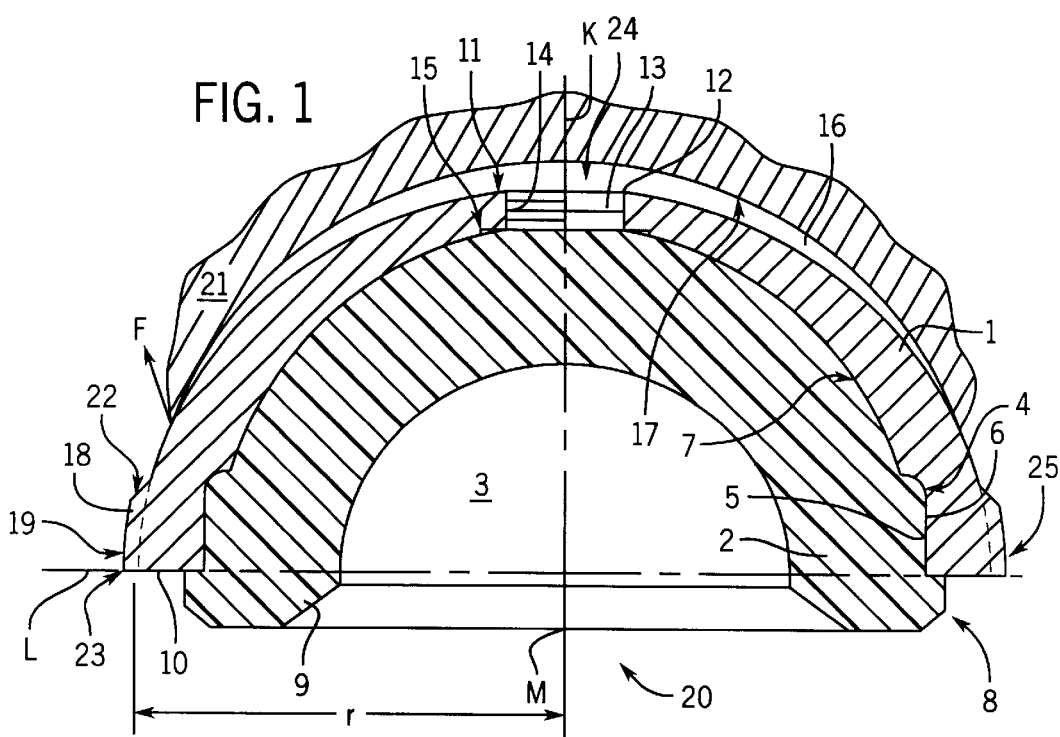
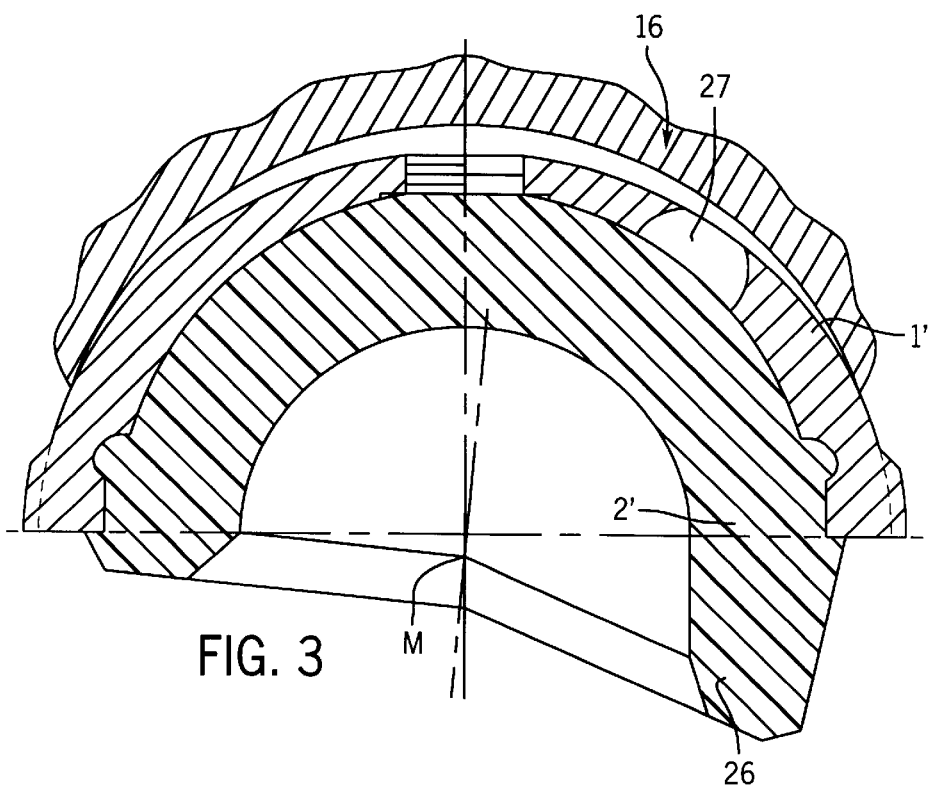

ELLIPTIC ACETABULAR COMPONENT FOR A HIP PROTHESIS

BACKGROUND OF THE INVENTION

The invention relates to a hip cup for use as an acetabular component in a hip prosthesis, comprising a shell part having an at least partially convex outer surface, which shell part can be inserted in a cavity having an inner surface that is substantially defined by the outer surface of a segment of a sphere.

The two techniques that are used most for attaching a hip cup concern the cemented and the uncemented technique respectively. In the cemented technique, the hip cup is fixed by means of bone cement. Within the uncemented technique, screw hip cups and press-fit hip cups are used. Screw cups are screwed into a cavity, which may or may not have been provided artificially in a bone, press-fit hip cups are for instance attached by knocking the hip cup into place in such cavity.

With these methods an attempt is made to approach the original anatomic situation as much as possible through the proper positioning of the acetabular component in the acetabulum. The position of the press-fit hip cup will change slightly in the first few months after positioning, due to the forces applied thereto. This change of position is commonly referred to as "settling".

For applying hip prostheses in patients, it is known to provide in an acetabulum a cavity having a truly spherical inner surface by means of a spherical cutter, wherein, subsequently, a press-fit hip cup is fittingly provided. Hence, this involves the outer surface of the hip cup abutting completely against the inner surface of the cavity formed, as a consequence of which, directly after the positioning of the hip cup, the forces acting on the hip cup are completely distributed on the inner surface of the cavity. The forces applied to the hip cup by the patient, particularly during movements of his leg, will cause the hip cup to slightly change position, especially in the first few months after positioning. Because the bone tissue around the hip cup will not have healed entirely yet in those months, and the hip cup will hence not have integrated entirely in the acetabulum yet, the hip cup will still be capable of moving somewhat, so that space will be created around the longitudinal edge of the hip cup. As the hip cup rests against the apex, it cannot be pressed any further into the cavity and will therefore become increasingly looser due to a cranial displacement, with all its consequences, in particular with regard to the patient's mobility. Moreover, this will cause the occurrence of high local peak loads.

SUMMARY OF THE PRESENT INVENTION

Hence, the object of the invention is to provide a hip cup of the type described in the opening paragraph, wherein the settling of the hip cup after positioning remains possible in an advantageous manner, without involving the occurrence of the above-mentioned peak loads and changes of position. To this end, the hip cup according to the invention is characterized in that the outer surface of the shell part substantially corresponds to the outer surface of a part of an ellipsoid, the arrangement being such that during positioning, the shell part contacts the longitudinal edge of the cavity at least by a circumferential edge, while a space is formed between the inner surface of the cavity and the apex of the shell part.

As the hip cup has an ellipsoid outer surface, it can be disposed in a spherical cavity with space, while a circumferential edge contacts the longitudinal edge of the cavity. As a result, when the hip cup is loaded in the first few months after positioning, the hip cup can advantageously be pressed somewhat further into the cavity, while the part of the convex outer surface of the hip cup that is contacted with the concave inner face of the cavity will become larger and larger. Due to the nature of the change of shape of the cavity and the shape of the hip cup, the transmission of forces from the hip cup to the acetabulum will largely be distributed on the periphery of the hip cup, as a result of which load peaks are avoided. Because the hip cup according to the invention has a flowing surface within the cavity, no tilting of the hip cup occurs, as it is guided along the inside of the cavity.

The elliptic form of the outer surface of the shell part has as a result that the space existing between the apex of the shell part and the inside of the cavity in the acetabulum is as small as possible, at least in the final position, and will moreover be filled relatively quickly and completely with the growth of new bone tissue, whereby an optimum, highly stable position of the hip cup in the acetabulum is obtained. In most cases, the anchoring of the hip cup in the acetabulum will hence be obtained entirely through press-fit, which has the advantage that no holes need to be drilled in the acetabulum and no screws need to be screwed therein. After all, the danger of such holes and screws is that in the case of an unfortunate location thereof, important nerves and veins and other vital parts of the body may easily be damaged, during positioning but also thereafter.

The part of the ellipsoid which defines the outer surface of the shell part is preferably formed through rotation of an ellipse around the short axis and the cutting of the thus formed ellipsoid approximately parallel to the circular section defined by the long axis of the ellipse. Such form is of a simple construction and moreover enables a particularly proper fit of the hip cup.

In a further elaboration of the hip cup according to the invention, the ratio between the short axis and the long axis of the ellipsoid surface is approximately between 0.9 and 0.975, and is preferably 0.925. For the usual dimensions of the hip cups, this means that the height/section ratio of the hip cup is optimal, while, moreover, the space is such that sufficient movement is possible for a proper settling of the hip cup and the space can still easily be filled with growth.

In a preferred embodiment of the hip cup according to the invention, the shell part is manufactured from titanium or a titanium-containing alloy, the outer surface of the shell part being at least partly porous. This embodiment has the advantage that the hip cup is biocompatible, so that rejection reactions of the body do not take place, while the porous surface enables the patient's bone tissue to partially grow in the outer surface of the hip cup, which further improves the adhesion between the hip cup and the acetabulum.

Preferably, the outer surface of the shell part is provided with a coating containing a calcium phosphate compound, preferably a hydroxyapatite. This will accelerate and further optimize the adhesion between the hip cup and the acetabulum.

The hip cup according to the invention preferably comprises an inner shell, fittingly insertable substantially within the shell part, which inner shell has an inner surface in the shape of a spherical shell and is manufactured from synthetic material, preferably from polyethylene. The inner shell forms a bearing surface for a hip head, to be rotatably accommodated therein, which hip head can be the natural as well as an artificial hip head. Because the inner shell is manufactured from synthetic material, good bearing properties with little friction and wear are obtained, and, moreover, a good damping of the forces applied to the hip head is obtained.

The invention further relates to a mounting tool to be used for positioning a hip cup in a cavity formed in an acetabulum, in particular suitable for use in a hip cup according to the invention. The mounting tool according to the invention is characterized in that the tool comprises a rod having at one end thereof an impact face and at the opposite end thereof fastening means, such as for instance screw thread, adapted for the positionally fixed, though detachable attachment of the hip cup to the tool, with a sleeve that can be fittingly arranged around the rod, which sleeve comprises a locating grip extending at an angle relative to the rod. With this mounting tool, the hip cup can be inserted in the cavity in an optimum manner through one or more blows on the impact face, the sleeve with the handgrip permitting a proper positioning of the rod so that the hip cup is driven into the cavity in the correct direction. As the hip cup can be fixedly mounted on the end opposite the impact face, the hip cup is prevented from changing position during positioning. The handgrip is provided, preferably at the end remote from the impact face, with a counter impact face, allowing the hip cup to be knocked out of the cavity as well by means of the mounting tool.

The invention further relates to a method for positioning a hip cup according to the invention, wherein, with a spherical cutter, a cavity is formed having a substantially spherical inner surface, whereupon the hip cup is placed on a mounting tool and contacted, by a longitudinal edge thereof, with the longitudinal edge of the cavity in such a manner that the short axis is held in the proper position for positioning the hip cup, whereupon, subsequently, the hip cup is knocked into the cavity by means of the tool in such a manner that a space is left open between the apex of the hip cup and the inner surface of the cavity, and the shell part of the hip cup, by a circumferential edge thereof, fixedly abuts against an inner longitudinal edge of the cavity, whereupon, subsequently, the tool is removed and, finally, a suitable inner shell is inserted in the shell part in the desired position.

Hereinafter, to explain the invention, an exemplary embodiment of the hip cup will be described, with reference to the accompanying drawings. In these drawings:

BRIEF DESCRIPTION OF THE DRAWINGS

FIG. 1 is a sectional view of a hip cup according to the invention, taken on the line I—I in FIG. 2;

FIG. 3 is a sectional view of an alternative embodiment of a hip cup according to the invention.

Figure 2:
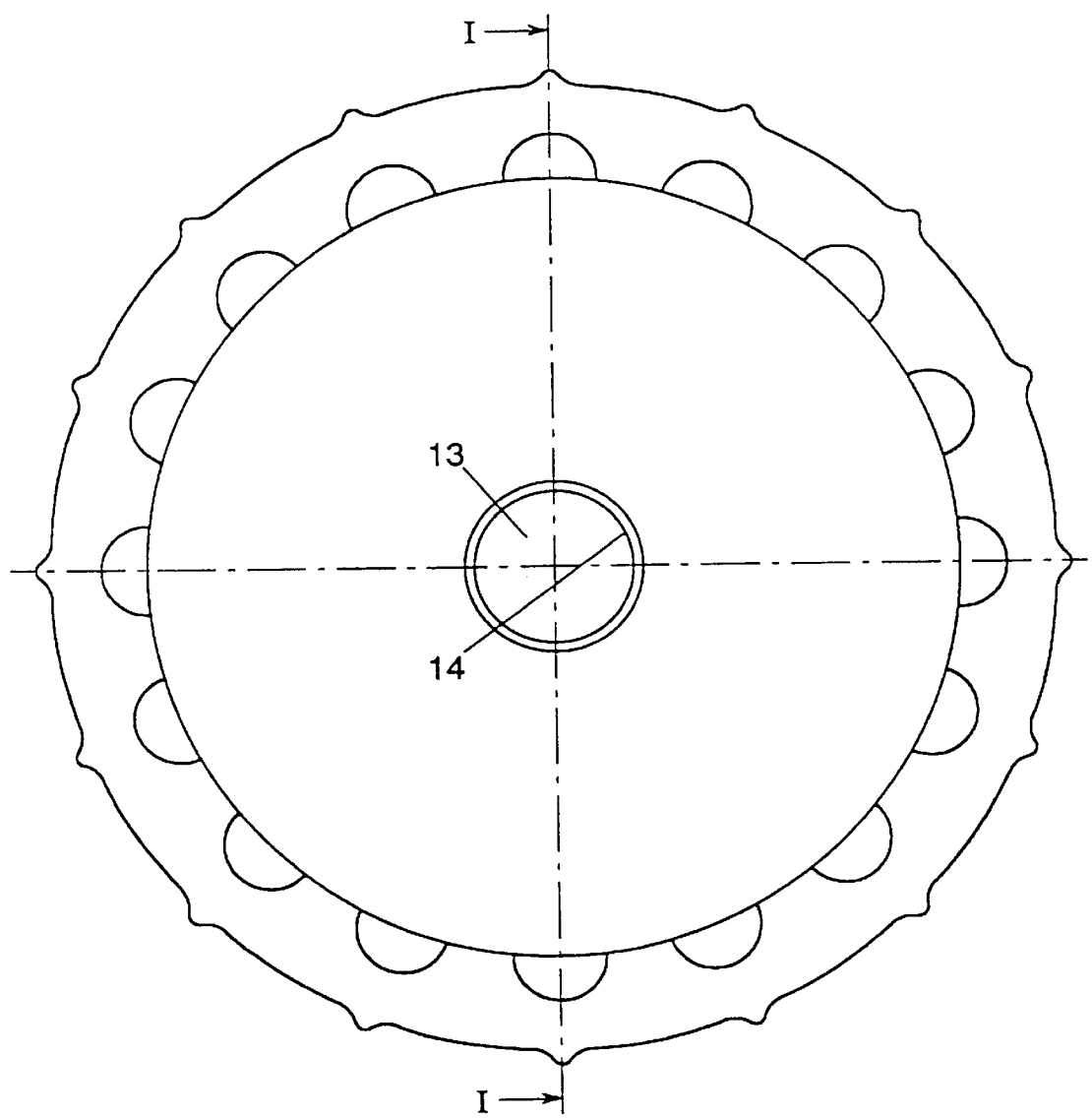
FIG. 2 is a view of the shell part of the hip cup according to the invention, from the open side.

The hip cup according to the invention, as shown in FIGS. 1 to 3, comprises an outer shell 1 and an inner shell 2, accommodated therein. The inner shell 2, preferably manufactured from synthetic material, such as polyethylene, has a spherical inner space 3, wherein a hip head which may or may not be natural, not shown in the drawing, can be received to form a hip joint. The inner shell 2 is provided, along its outer surface 4, with four evenly distributed lugs 5, which extend substantially radially from the outer surface and can each be received in one of sixteen evenly distributed recesses 6 provided in the inner surface 7 of the outer shell 1. Along the outer longitudinal edge 8, the inner shell 2 is provided with a stop shoulder 9 extending outside the outer shell 1 and covering at least a portion of the lower edge 10 of the outer shell 1.

The inner shell 2 can be fittingly accommodated in the outer shell 1 such that the entire outer surface 4 of the inner shell 2 contacts the inner surface 7 of the outer shell, while the lugs 5 are tightly accommodated in the recess 6. The inner shell 2 can be disposed in sixteen different positions relative to the outer shell 1, depending on which recesses 6 the lugs 5 are received in. This is particularly important if the inner shell 2 is not symmetrical relative to all planes passing through the center line M, as is for instance the case in the structural variant shown in FIG. 3, as will be further explained hereinbelow.

The outer shell 1 has an ellipsoid outer surface 11, which outer surface is described by a body of revolution obtained through rotation of an ellipse around the short axis K. In FIG. 1, this short axis coincides with the center line M of the inner shell 2. The ratio of the short axis K relative to the long axis L of the ellipsoid is approximately between 0.9 and 0.975, and preferably approximately 0.925. For hip cups of a usual dimension, for instance approximately 50 mm in section, this means that the short axis K is approximately 3.75 mm shorter than the long axis L. Hence, in the dimensional example given, the maximum height of the outer shell 1 is approximately 1.875 mm smaller than the radius R of the circle described by the long axis L of the ellipsoid.

From the outer surface 11 of the outer shell 1, sixteen fins 18, evenly distributed on the circumference, extend outward, which fins 18 have a somewhat sharp outer edge 19.

On the top side, and preferably in the apex 12 of the outer shell 1, an opening 13 is provided having an internal screw thread 14. Provided around this opening 13 and on the inside of the outer shell 1 is a flat, annular recess 15, extending at right angles to the short axis K. By means of the screw thread 14, the outer shell 1 can be mounted on a mounting tool, as will be further explained hereinafter.

Figure 4:
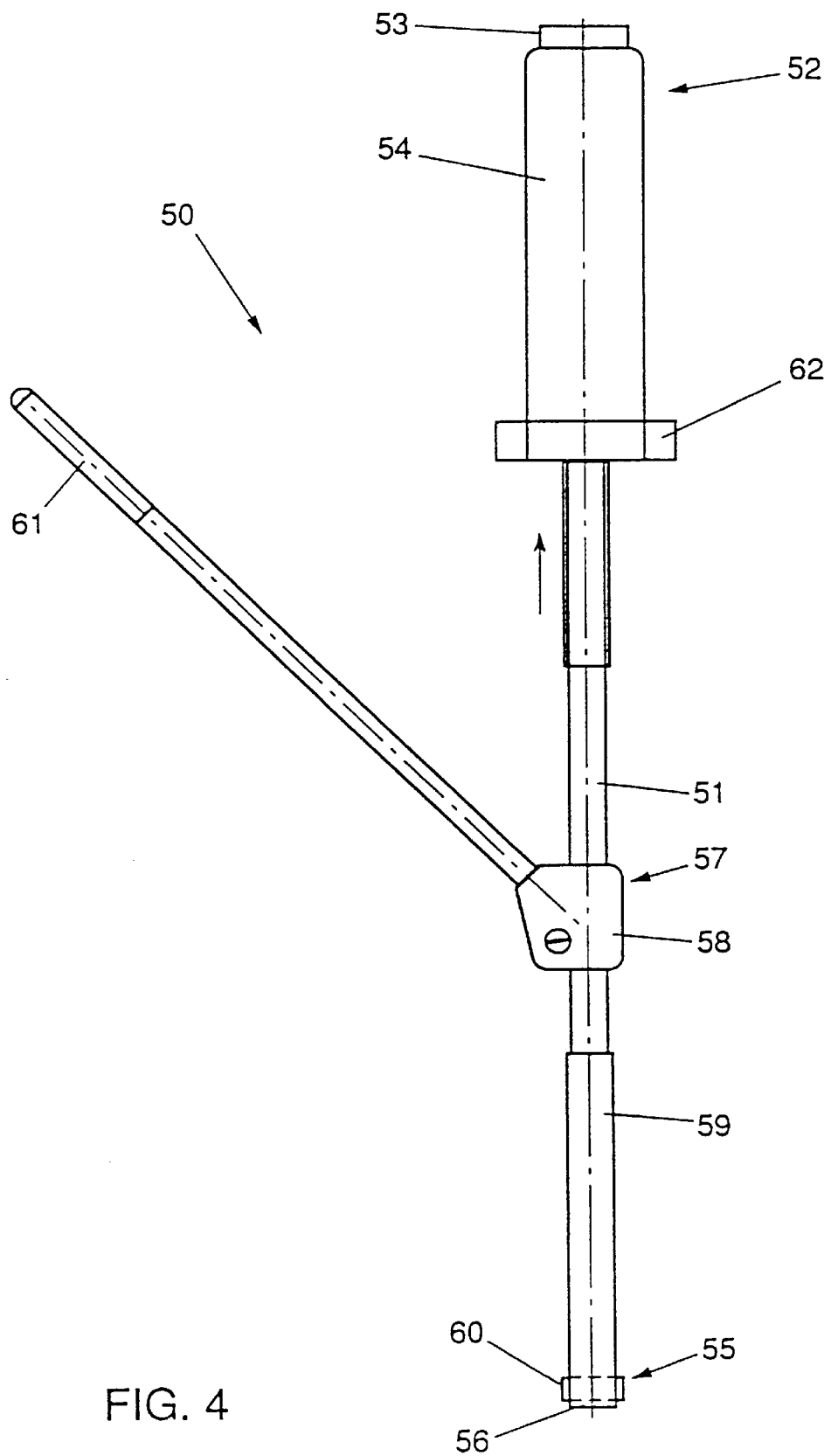
FIG. 4 shows a mounting tool according to the invention.

The mounting tool 50, as shown in FIG. 4, comprises a rod 51, having at one end 52 thereof an impact face 53 and a handgrip 54, and, at the other end 55 thereof, an outer screw thread 56 capable of cooperating with the screw thread 14 in the opening 13 in the hip cup. At the end remote from the impact face 53, the handgrip 54 comprises a counter impact face 62. On the side of the screw thread 56 remote from the adjacent end 55 is a stop collar 60, at a distance from that end 55 which approximately corresponds to the thickness of the outer shell 1 at the level of the apex 12. The stop collar 60 has an outer diameter corresponding to the diameter of the annular recess 15 provided around the hole 13 in the outer shell 1. Over the middle portion 57 of the rod 51, a sleeve 58 can be arranged over the rod 51. The middle portion on which the sleeve can be arranged is bound on the one hand by the handgrip 54 and on the other by a thickening 59 provided on the rod 51. From the sleeve 58, in the disposed condition, a locating grip 61 extends in an inclined manner relative to the longitudinal axis of the rod 51, in the direction away from the stop collar 60.

A hip cup according to the invention can be inserted in an acetabulum as follows.

In an acetabulum 21 of a patient whose existing, natural hip cup is no longer suitable for use, due to for instance a disease or trauma, a spherical cavity 16 is provided by means of a spherical cutter, and the sphere describing the inner face 17 of the cavity 16 has a center line corresponding to the length of the long axis L. By means of the screw thread 14 in the opening 13, the outer shell 1 is fixedly screwed onto the screw thread 56 on the end 55 of the rod 51, with the open side in the direction of the rod 51. The outer shell 1 is screwed onto the rod far enough for the stop collar 60 to contact the annular recess 15. As a result, the outer shell is mounted on the end of the rod 51 in a fixed position, allowing the outer shell 1 to be inserted in the cavity 16. As a matter of fact, the outer shell can also be mounted on the rod by means of for instance clamping or like means.

By the side 22, facing away from the open side 20, of at least a number of fins 18, the outer shell is contacted with the outer longitudinal edge 23 of the cavity 16, while the outer shell 1 is held in the proper position by means of the mounting tool 50. Subsequently, one or more blows are given to the impact face 53 by means of a hammer or the like, in such a manner that the outer shell 1 is driven into the cavity, the fins 18 cutting into the acetabulum around the cavity 16. The rod 51 now lies at least temporarily within the sleeve 58, brought into the desired position by means of the locating grip 61, which ensures that the outer shell 1 is inserted in the cavity 16 in the correct position. In the embodiment shown in FIG. 1, this means that the short axis K of the outer shell 1 is parallel to the axis of symmetry of the cavity 16, but it is equally possible to arrange the outer shell 1 in a slightly rotated position relative to this axis of symmetry, for instance for the purpose of a positional correction, as shown in FIG. 3.

The outer shell 1 is driven into the cavity 16 far enough for the lower edge 10 thereof to be approximately level with the outer longitudinal edge 23 of the cavity 16, leaving a space 24 between the apex 12 of the outer shell 1 and the inner surface 17 of the cavity 16. Hence, the outer shell 1 contacts the inner surface 17 of the cavity 16 only by a portion 25 of the outer surface 11 which extends close to the lower edge 10, with the fins 18 extending into the acetabulum 21, ensuring that the outer shell 1 does not rotate around the short axis K. Subsequently, the mounting tool 50 is removed from the opening 13.

After the outer shell 1 has thus been disposed in the cavity 16 at the proper location and in the proper position, the inner shell 2 is pressed in the desired position into the outer shell 1, the lugs 5 being received in the proper recesses 6, in such a manner that the inner shell 2 is fixedly connected to the outer shell 1 and the hip cup is ready. Subsequently, the corresponding hip head can be received in the inner space 3 of the inner shell 2.

Due to the load of the hip cup 1 in the first few months after positioning, and the fact that the bone tissue enclosing the cavity 16 has not yet completely healed and grown in that period, the hip cup will be pressed somewhat further into the cavity 16, the so-called settling. Because the outer surface 11 of the outer shell 1 is ellipsoid and the space 24 is therefore left clear, the hip cup can be pressed further into the cavity 16, the inner shape of the cavity 16 becoming slightly ellipsoid. By the outer surface 11, the outer shell 1 can simply slide along the inner surface 17 of the cavity 16. As a result, the hip cup will be fixed in the acetabulum 21 more properly. Moreover, initially after positioning, a part of the forces applied to the hip cup can be transmitted by the caudal side of the hip cup to the acetabulum, as indicated by the arrow F in FIG. 1.

If the outer shell is truly spherical, as is the case in many known hip cups, this is not possible (or only to a very small extent), because the outer shell then has its apex abutting against the inner surface of the cavity, while along at least the caudal part of the longitudinal edge space is created due to the (changing) load, causing an unfavorable distribution of forces on the hip cup.

Due to the forces applied to the hip cup when the hip cup settles in the first few months after positioning, a slight yet relevant change of shape of the cavity is effected, the inner surface of the cavity becoming slightly ellipsoid. Consequently, the hip cup according to the invention will fit increasingly better in the cavity.

In the first few months after positioning, the space 24 will be filled through the growth of bone tissue, which even further improves the fit of the hip cup. The outer shell 1 is manufactured from a titanium alloy with a porous top layer, and a coating is applied containing a calcium hydroxyapatite. Due to the coating, the bone growth toward the outer shell 1 will be promoted, and the bone will grow slightly into the porous top layer. In addition, the outer shell 1 is sufficiently strong to withstand the forces applied thereto and is moreover biocompatible.

The inner shell 2 is manufactured from polyethylene, which simultaneously yields proper sliding properties and a damping action on the forces to be transmitted by the hip head to the hip cup, as a result of which high load peaks will be smoothed out.

In the structural variant of the hip cup shown in FIG. 3, the inner shell 2' is provided with an antiluxation edge 26, projecting outside the outer shell 1' and approximately extending along the half of the circumferential edge 9' of the inner shell 2' that is located on the cranial side. The antiluxation edge 26 increases in height in the direction of the cranial side, and is intended to prevent a luxation of the hip head relative to the hip cup. Moreover, the inner shell 2' is provided with the line of symmetry M' slightly inclined relative to the short axis K of the outer shell 1', for instance for the purpose of correcting the position of the maximum freedom of movement of the patients leg. When such an inner shell 2' is used, it is particularly advantageous that it can be disposed in sixteen positions within the outer shell 1', because this permits a simple correction of small deviations of the position of the outer shell 1' relative to the acetabulum 21.

It will further be understood that, in principle, any number of recesses 6 in the outer shell 1, 1' is possible, as long as the number at least corresponds to the number of lugs 5 on the inner shell 2, 2' and the distribution thereof enables the lugs 5 to be received in the recesses 6. For a stable positioning, it is desirable that at least two, but preferably more than two lugs 5 are used, provided diametrically opposite one another.

In the structural variant shown in FIG. 3, the outer shell 1' is provided, on the cranial side thereof, with a recess 27, wherein the head of a fixing screw to be used, optionally, can be received. Such a fixing screw is intended to provide better stability of the hip cup within the acetabulum, and for this purpose, it is screwed through the outer shell 1' into a hole provided in the acetabulum 21. However, for the great majority of uses of the hip cup according to the invention, such a fixing screw is superfluous, because due to the press fit, the outer shell 1, and hence the hip cup as a whole, can be mounted in the acetabulum 21 so as to be sufficiently stable.

If the hip cup should be removed from the cavity, for instance because of a correction to be carried out, the mounting tool 50 can be placed back in the opening 13, after which the hip cup can be knocked out of the cavity by striking the counter impact face with a hammer or a like tool.

The invention is not limited to the embodiments depicted in the drawings and specification. Many other embodiments are possible within the scope of the invention. For instance, other means can be used for anchoring the outer shell against rotation, such as nails or screws driven into the bone, differently shaped fins or, for instance, lugs or like projections provided in several rows over a substantial portion of the outer surface. Further, the inner shell can be designed in all sorts of different ways, depending on the desired possibilities of movement of the patient, and on the desired mounting method of the inner shell in the outer shell. For instance, the center of rotation of the hip cup within the hip cup can be shifted by adjusting the shell shape of the inner shell, and the inner shell can be secured in the outer shell in various manners other than the manner shown.

What is claimed is:

1. A hip cup for use as an acetabular component in a hip prosthesis of a patient having a bone cavity including an inner surface configured as a segment of spherical surface and which includes a peripheral portion, said cup comprising an outer shell having a partially convex outer surface and a circumferential edge portion and having an apex and a central cross-section and forming one half of an ellipse with a short radius through the apex and a long radius at the peripheral portion, the outer shell being configured for insertion into the bone cavity, said circumferential edge portion of the outer surface of the outer shell upon insertion into said cavity contacts said peripheral portion of the cavity and is configured to form a space between the inner surface of the cavity and the apex of the outer shell, said outer surface of the outer shell being defined by rotation of said ellipse about said short radius and having a cross section in a plane containing the long radius of the ellipse to form a half rotational ellipsoid, the ratio between the length of the short radius between said apex and said long radius and the length of the long radius within the ellipse is approximately between 0.9 and 0.975.

2. The hip cup of claim 1, wherein the hip cup comprises means (18) projecting outwardly from the shell surface, said means providing for the rotationally fixed attachment of the outer shell (1) in said bone cavity.

3. The hip cup according to claim 1, wherein the outer surface (11) of the outer shell (1) is biocompatible and promotes osteo-integration over at least a portion of the outer surface.

4. The hip cup according to claim 3, wherein the body of the outer shell (1) selected from the group of titanium or a titanium-containing alloy.

5. The hip cup according to claim 3, wherein the outer surface (11) of the outer shell (1) is at least partly porous.

6. The hip cup according to claim 3, wherein the outer surface (11) of the outer shell (1) is provided with a coating containing a calcium phosphate compound.

7. The hip cup of claim 1 comprising an inner shell (2) fittingly insertable substantially within the outer shell (1), said inner shell (2) having an inner surface in the shape of a spherical shell.

8. The hip cup according to claim 7, wherein the inner shell (2) is a synthetic material.

9. The hip cup according to claim 7, wherein the inner shell and said outer shell include means to support the inner shell in the outer shell in a number of relative rotational positions.

10. The hip cup according to claim 7, wherein the inner shell comprises an antiluxation edge, said edge extending outside the outer shell.

11. The hip cup of claim 1, wherein the outer shell includes at least one opening having a fastening means for receiving a mounting tool.

12. The hip cup of claim 6, wherein said compound is a hydroxyapatite.

13. The hip cup of claim 8, wherein said synthetic material is polyethylene.

* * * * *

UNITED STATES PATENT AND TRADEMARK OFFICE
CERTIFICATE OF CORRECTION

PATENT NO.   : 6,059,833
DATED         : May 9, 2000
INVENTOR(S) : Hendrik Cornelis Doets Page 1 of 1

It is certified that error appears in the above-identified patent and that said Letters Patent is hereby corrected as shown below:

Claim 2, Column 8,
Line 2, Delete "(18)";
Line 2, Delete "shell" and substitute therefor -- outer --;
Line 2, After "surface" insert -- of said shell --;
Line 3, Delete "providing for the" and substitute therefor -- configured to establish --;
Line 4, Delete "(1)";

Claim 4, Column 8,
Lines 9-10, Delete "the body of the" and substitute therfor -- said ;
Line 10, After "(1)" insert -- is of material --;
Line 10, Delete "or" and substitute therfor -- and --;

Claim 7, Column 8,
Lines 17-18, Delete "(2) fittingly";
Line 18, Delete "(1)";
Line 19, Delete "(2)";
Line 19, After "inner" insert -- spherical --;
Lines 19-20, After "surface" delete "in the shape of a spherical shell";

Claim 8, Column 8,
Line 11, Delete "(2)".

Signed and Sealed this

Fourth Day of September, 2001

*Attest:*

Nicholas P. Godici

NICHOLAS P. GODICI
*Attesting Officer*     *Acting Director of the United States Patent and Trademark Office*